United States Patent [19]

Hilleman et al.

[11] 4,000,256
[45] Dec. 28, 1976

[54] VARICELLA VACCINE AND PROCESS FOR ITS PREPARATION

[75] Inventors: Maurice R. Hilleman, Lafayette Hill; Eugene B. Buynak, North Wales; Beverly J. Neff, Harleysville, all of Pa.

[73] Assignee: Merck & Co., Inc., Rahway, N.J.

[22] Filed: July 2, 1975

[21] Appl. No.: 592,562

Related U.S. Application Data

[63] Continuation-in-part of Ser. No. 573,296, April 30, 1975, abandoned, which is a continuation-in-part of Ser. No. 415,476, Nov. 13, 1973, abandoned.

[52] U.S. Cl. .................................. 424/89; 195/1.3
[51] Int. Cl.$^2$ ................. A61K 39/12; C12K 5/00; C12K 7/00

[58] Field of Search ...................... 424/89; 195/1.3

[56] References Cited
OTHER PUBLICATIONS

Andrewes et al., Viruses of Vertibrates, 2nd edition, (1967), pp. 291, 292.

*Primary Examiner*—Sam Rosen
*Attorney, Agent, or Firm*—Donald J. Perrella; Julian S. Levitt

[57] ABSTRACT

Preparation of safe, live, attenuated varicella virus vaccine by serial propagation of varicella virus in tissue cell culture systems.

20 Claims, No Drawings

VARICELLA VACCINE AND PROCESS FOR ITS PREPARATION

CROSS-REFERENCE TO PRIOR APPLICATIONS

This application is a continuation-in-part of United States application Ser. 573,296 filed Apr. 30, 1975, now abandoned, which in turn is a continuation-in-part of United States application Ser. No. 415,476 filed Nov. 13, 1973, now abandoned.

This invention relates to a vaccine against Varicella and to methods for the preparation of such a vaccine.

In particular the invention relates to a safe, live, attenuated varicella virus vaccine and a method of producing the vaccine by serial propagation of varicella virus in cell culture systems.

Varicella, or chicken pox, is a highly communicable disease primarily of childhood. The illness is characterized typically by fever and development of a macular rash which rapidly evolves through stages of papule, and vesicle formation. Recovery is usually without incident, but the disease even in its mild form is unsightly and can result in considerably scarring from ruptured vesicles. In some cases, the illness may be quite severe in that primary varicella pneumonia may occur in children or adults. Central nervous system complications such as acute cerebellar ataxia with tremors and muscular hypotonia may precede, accompany, or follow varicella infection. More rarely, there is generalized involvement of the central nervous system with hemorrhage, perivascular round cell infiltration, and demyelinization. Neuristis and myelitis may also occur. The skin involvement may also be troublesome with appearance of hemorrhagic, bulbous or gangrenous lesions.

Thus prevention of the disease by vaccination is justified to preclude such events, and it is an object of this invention to provide a safe, live, attenuated varicella virus vaccine for this purpose and a process for its preparation.

Several investigators, in the past, have attempted vaccination of susceptible human volunteers with variable results with respect to "takes", and much disagreement concerning the protective efficacy. However, there was a lack of significant untoward effects in spite of the fact that these attempted vaccinations were of susceptible volunteers with fully virulent virus in vesicular fluid from varicella-zoster cases.

The prior art has reported the propagation of varicella in various cell culture systems such as human amnion, human embryo fibroblasts, HeLa cells and human thyroid, but prior to this invention it was generally believed that the only source of viable, cell-free varicella virus was vesicular fluid. Caunt et al., *Journal of Hygiene*, 62, 413–424 (1964) reported the isolation of cellfree virus from human thyroid tissue and Brunnel, *Virology*, 31, 732-4 (1967) described the isolation of cell-free virus from human embryo fibroblasts. Vesicular fluid is obviously an unsuitable source of live virus for production of a vaccine because of the limited supply and virulence. Human thyroid tissue is a primary human cell-line, and hence unacceptable as a tissue culture system for the propagation and attenuation of viruses for the production of live virus vaccines.

Surprisingly, it now has been discovered that cell-free passage can be achieved in suitable tissue culture preparations, extra-cellular living varicella virus useful as an antigen can be obtained in quantity, and a live attenuated varicella vaccine which will evoke in man an antibody response against a virulent varicella virus without causing the severe clinical manifestations of the disease can be prepared therefrom.

The process of this invention comprises serial passage of virulent varicella virus in a tissue culture system. The tissue culture system can be any one suitable for vaccine production and known to support growth of the virus, such as human diploid cell strains as exemplified by WI-38 and MRC-5, animal diploid cell strains (fetal rhesus) and primary cells of simian origin. The preferred systems are of monkey testicular tissue and diploid human fetal lung tissue such as WI-38 prepared by known methods.

The culture is incubated at 36°–38° C. for from 3 to about 5 days. After inoculation, the actual time of incubation varies and is determined by the extent of viral propagation as indicated by microscopic observation (e.g. CPE). The inoculum can be an infected cell suspension or virus released by methods such as sonication. Incubation of the infected culture can be in the temperature range of 30°–38° C.

When the appropriate degree of infectivity is observed, usually after from about 10 to about 80 serial passages of the virus, the maintenance fluids are aseptically removed. It should be noted that the number of serial passages required may depend upon the particular isolate or source of virus utilized in the preparation of the vaccine. The cell sheets are then rinsed several times with a serum-free physiological solution such as phosphate buffer, saline (PBS) or Hanks balanced salt solution. A suitable stabilizer such as a composition comprised of sucrose, albumin, glutamine and phosphate or the like is added in a volume of from about 5 to 30% of the original fluid volume.

The infected cells are removed from the vessel surface into the stabilizer medium by appropriate means (e.g. freeze-thawing or cell scraping). The stabilizer-cell suspensions are then pooled and the infected cells are further disrupted by appropriate means such as sonication. The resultant disrupted suspension is then clarified by filtration to remove the cell debris to insure a cell-free virus preparation. The resultant virus preparation is then subdivided into a suitable container for distribution as a vaccine. The dose can be from about 0.1 to about 2.0 ml. containing from 100 to about 5000 infective units in flame-sealed ampules, or as a freeze-dried product in stoppered vials ready for reconstitution in sterile water. Administration can be by scarification (multiple puncture) intradermal, or subcutaneous routes.

The seed virus for the above process is isolated in vesicle fluid from a clinical case of chicken pox and stored in veal infusion broth at −70° C.

EXAMPLE 1

Live attenuated, cell free varicella vaccine prepared by 20 serial passages in WI-38

Nineteen serial passages of varicella virus in WI-38 tissue culture was conducted as follows:

Initial isolation of varicella virus was made from a vesicle fluid specimen obtained from a child with clinical chicken pox. The vesicle fluid specimen was collected in veal infusion broth and stored at −70° C; at the time of isolation the specimen was thawed, diluted with an equal volume of veal infusion broth containing 100 mcg of neomycin and 100 mcg of polymixin per ml and incubated for 30 minutes at 25° C. The specimen was inoculated into established WI-38 cell cultures of human fetal diploid origin and incubated at 32° C., thus constituting passage one of a set of serial sub-cultures.

Progressive cytopathology typical of varicella was observed and when sufficiently advanced (3–13 days post inoculation) the overlying fluids were decanted and the infected cells harvested by known trypsinization techniques. Following removal of trypsin by centrifugation, the cells were resuspended, counted and re-inoculated to a fresh set of WI-38 cell cultures, constituting the second serial passage at 32° C. Subsequent passages of infected cell suspensions continued in the same fashion. Passage of virus could also be initiated from infected cell suspensions stored at −70° C. with cryogenic protective additives such as glycerol, sorbitol or DMSO, known to preserve cell viability.

Using an infected cell suspension of the 19th passage as seed virus, a live attenuated cell free varicella vaccine was prepared as follows:

WI-38 cell cultures were prepared in glass roller bottles using EBME, a commercial preparation of Eagle's medium in Earle's basal salt solution containing 10% unheated fetal calf serum as growth medium. Two days post-planting, the growth medium was discarded and bottle cultures were inoculated with approximately $2 \times 10^6$ infected cells per bottle and refed with 100 ml. of EBME containing 2% inactivated agamma calf serum.

Three days post inoculation the system was refed with 100 ml. of EMBE containing 2% inactivated agamma calf serum. Incubation was at 32° C. in a rolling apparatus. Seven days post-seeding, the bottle cultures were rinsed two times with phosphate buffer saline, 100 ml. per rinse. Sixteen ml. of SPGA stabilizer was added to each bottle. The SPGA stabilizer is comprised of the following:

| Sucrose | 74.621 | grams |
| Mono-potassium phosphate | 0.45 | grams |
| Di-potassium phosphate | 1.35 | grams |
| Mono-sodium L-glutamate | 0.956 | grams |
| Human albumin (25% solution of albuminsol) | 40 ml. | |
| Sterile distilled water | q.s. to one liter | |

The stabilizer is prepared by dissolving the ingredients in 800 ml. of sterile distilled water and bring up the volume to one liter with additional distilled water. The pH of the composition should be between 6.9–7.1. Neomycin at a concentration of 50 mcg/ml was incorporated in the growth, rinse, maintenance and stabilizer media. Infectivity titrations of each harvest were performed in WI-38 cell cultures.

After addition of the stabilizer, contents of individual bottles were shell-frozen in a $CO_2$-alcohol bath (ca. −70° C.). The frozen contents of the bottles were rapidly thawed with vigorous shaking, partially disrupting the cell sheet and releasing the cells into the fluid stabilizer. The bottle contents were pooled, sampled for sterility and infectivity (determined after batch sonication of a small sample) and stored at −70° C. in a mechanically-operated freezer. Three weeks later, when preliminary sterility and infectivity tests were satisfactory, the pooled stabilizer-cell suspensions were rapidly thawed and transferred to a flow sonication apparatus.

Alternatively, storage of the pooled stabilizer-cell suspension at −70° C. could be omitted and the process continued with flow sonication and filling completed in a single continuous operation.

The flow sonication apparatus had the following components:

1. Sonifier cell disruptor and attachments (wattmeter, ½ inch tapped disruptor horn and stainless steel continuous flow attachment),
2. Special water-jacketed four liter pyrex glass vessel;
3. Heat exchanger of stainless steel tubing, spirally wound and jacketed;
4. Refrigerated bath and circulator;
5. Flowmeter; and
6. Micro-pump, variable speed.

The conditions of operation were:

1. Power input: 120 watts as shown on the ultrasonic wattmeter attachment;
2. Flow rate: 150 ml/min. (measured on flowmeter and controlled externally by the micro-pump);
3. Cycles of sonication: four, e.g. total volume displaced through the sonicator four times; and
4. Temperature of operation: 0°–4° C.

The continuous flow attachment, 4-liter holding vessel, heat exchanger, flowmeter and the micro-pump intake were assembled as a unit before use and sterilized. External connections between the refrigerated circulating bath and the jacketed portions of the apparatus allowed the entire apparatus to be chilled to 0°–4° C. and maintained at that temperature throughout the sonication process.

Following sonication, which resulted in essentially 100% cell disruption, the pre-clarified bulk vaccine was sampled for control and safety testing. The remaining vaccine was clarified by filtration through a 1 inch by 8 inches medium (15 micron) porosity sintered glass filter candle and collected in a pre-chilled container. Prior to use, the candle-filter was primed with one liter of stabilizer. Post-clarification samples were removed for animal safety testing and a 50 ml. sample was centrifuged and the sediment resuspended in 0.5 ml. of stabilizer (hundred-fold concentrate) and transferred to slides for microscopic examination for presence of intact cells. None were observed.

The final cell-free, live varicella vaccine is dispensed in 0.7 ml. – 1.2 ml. amounts and frozen at −70° C. or frozen at −70 C. in rubber stoppered vials for subsequent preservation by lyophilization, employing techniques well known to the art, including methods set forth in Calnek et al., *Applied Microbiology*, November 1970, Vol. 20, No. 5, pgs. 723–726. A convenient method of lyophilization is as follows:

Starting with the pre-frozen samples (−70° C.) and a processing chamber pre-cooled to −40° C., the chamber is evacuated to a pressure of 175 microns Hg. The drying cycle is initiated by raising the temperature to −10° C. and maintaining the samples at −10° C. for 1 hour. During the next 90 minutes, the temperature is gradually increased to +30° C. and the samples are held at this temperature for 19½ hours. At the end of the process, the vacuum is released by introduction of an inert gas, Argon, and the sample vials are automatically stoppered.

Infectivity was demonstrated in wet-frozen (−70° C.) or lyophilized vaccine preparations for at least 6 months following preparation.

A convenient dosage form may be prepared by reconstituting the lyophilized material to the original fill (0.7—1.2 ml.) by the addition of sterile distilled water and employing from about 0.1 ml. to 1.0 ml. of said reconstituted material for parenteral administration as a varicella vaccine. The wet-frozen form of the vaccine which contains 0.7 to 1.2 ml. of vaccine may be thawed prior to use with a dosage of from about 0.1 ml. to 1.0 ml. of the vaccine being administered parenterally.

EXAMPLE 2

Live attenuated, cell free varicella vaccine prepared by 15 serial passages in WI-38

A live attenuated, cell free varicella vaccine is prepared by employing the procedure substantially as described in Example 1, except that a total of 15 passages in WI-38 tissue culture is performed.

EXAMPLE 3

Live attenuated, cell free varicella vaccine prepared by 15 serial passages in WI-38

A live attenuated, cell free varicella vaccine is prepared by employing the procedure substantially as described in Example 1 except that the following six serial passage levels at 32° C., a new series of passages at 36° C. was initiated at the seventh passage level and continued at 36° C. through the 14th passage level for preparation of a vaccine at the 15th passage.

EXAMPLE 4

Live attenuated, cell free varicella vaccine prepared by 20 serial passages in WI-38

A live attenuated, cell free varicella vaccine is prepared by employing the procedure substantially as described in Examples 1 and 3 except that following six serial passage levels at 32° C., a new series of passages at 36° C. was initiated at the seventh passage level and continued at 36° C. through the 19th passage level for preparation of a vaccine at the 20th passage.

EXAMPLE 5

Live attenuated, cell free varicella vaccine prepared by 30 serial passages in WI-38

A live attenuated, cell free varicella vaccine is prepared by employing the procedure substantially as described in Examples 1 and 3 except that following six serial passage levels at 32° C., a new series of passages at 36° C. was initiated at the 7th passage level and continued at 36° C. through the 29th passage level for preparation of a vaccine at the 30th passage.

EXAMPLE 6

Live attenuated, cell free varicella vaccine prepared by 40 serial passages in WI-38

A live attenuated, cell free varicella vaccine is prepared by employing the procedure substantially as described in Examples 1 and 3 except that following six serial passage levels at 32° C., a new series of passages at 36° C. was initiated at the seventh passage level and continued at 36° through the 39th passage level for preparation of a vaccine at the 40th passage.

EXAMPLE 7

Live attenuated, cell free varicella vaccine prepared by 20 serial passages in monkey testicular cell tissue culture A live attenuated, cell free varicella vaccine is prepared by employing the procedure substantially as described in Example 1 except that a known monkey testicular cell tissue culture is used in place of the WI-38 culture system, with a total of 20 serial passages.

EXAMPLE 8

Live attenuated, cell free varicella vaccine prepared by 20 serial passages in monkey testicular cell tissue culture A live attenuated, cell free varicella vaccine is prepared by employing the procedure substantially as described in Example 3 except that a known monkey testicular cell tissue culture is used in place of the WI-38 culture system, with a total of 20 serial passages.

EXAMPLE 9

Live, Attenuated, Cell-Free Varicella Vaccine Prepared by 30 Serial Passages in WI-38

A live, attenuated, cell-free varicella vaccine is prepared by employing the procedure substantially as described in Example 1 with the exception that following six serial passage levels at 32° C., a new series of passages at 36° C. is initiated at the 7th passage level and continued at 36° C. through the 29th passage level.

Using an infected cell suspension of the 29th passage as seed virus, a live attenuated cell-free varicella vaccine is prepared as follows:

WI-38 cell culture were prepared in glass roller bottles using EBME, a commercial preparation of Eagle's medium in Earle's basal salt solution containing 10% unheated fetal calf serum as growth medium. Two days post-planting, the growth medium is discarded and bottle cultures are inoculated with approximately 2 × $10^6$ infected cells per bottle and refed with 100 ml. of EBME containing 2% inactivated agamma calf serum. Three days post inoculation the system is refed with 100 ml. of EMBE containing 2% inactivated agamma calf serum. Incubation is at 36° C. in a rolling apparatus. Seven days post-seeding, the bottle cultures are rinsed four times with phosphate buffer saline, 100 ml. per rinse. Twenty ml. of SPGA stabilizer prepared according to Example 1 is added to each bottle.

After addition of the stabilizer, contents of individual bottles are shell-frozen in a $CO_2$-alcohol bath (ca. −70° C.). The frozen contents of the bottles were rapidly thawed with vigorous shaking, partially disrupting the cell sheet and releasing the cells into the fluid stabilizer. The bottle contents are pooled, sampled for sterility and infectivity (determined after batch sonication of a small sample) and stored at −70° C. in a mechanically-operated freezer. Three weeks later, when preliminary sterility and infectivity tests are satisfactory, the pooled stabilizer-cell suspensions are rapidly thawed and transferred to a flow sonication apparatus and sonicated according to the procedure set forth in Example 1.

Alternatively, storage of the pooled stabilizer-cell suspension at −70° C. could be omitted and the process continued with flow sonication and filling completed in a single continuous operation.

Following sonication, which results in essentially 100% cell disruption, the pre-clarified bulk vaccine is sampled for control and safety testing. The remaining vaccine is clarified by filtration through a 1 inch by 8 inches medium (15 micron) porosity sintered glass filter candle and collected in a pre-chilled container. Prior to use, the candle-filter is primed with one liter of stabilizer. Post-clarification samples are removed for animal safety testing and a 50 ml. sample is centrifuged and the sediment resuspended in 0.5 ml. of stabilizer (hundred-fold concentrate) and transferred to slides for microscopic examination for presence of intact cells. None are observed.

The final cell-free, live varicella vaccine is dispensed in 0.7 ml.–1.2 ml. amounts and frozen at −70° C. or frozen at −70° C. in rubber stoppered vials for subsequent preservation by lyophilization, as set forth in Example 1.

Infectivity is demonstrated in wet-frozen (−70° C.) or lyophilized vaccine preparations for at least 6 months following preparation.

EXAMPLE 10

Live, Attenuated, Cell-Free Varicella Vaccine Prepared By 40 Serial Passages in WI-38

A live, attenuated, cell-free varicella vaccine is prepared by employing the procedure substantially as described in Example 9 except that following six serial passage levels at 32° C., a new series of passages at 36° C. is initiated at the 7th passage level and continued at 36° C. through the 39th passage level for preparation of a vaccine at the 40th passage.

What is claimed is:

1. A process for the preparation of a live attenuated, cell-free varicella virus useful as an antigen in a vaccine, which will evoke in man an antibody response against a virulent varicella virus without causing the severe clinical manifestations of the disease which comprises serially passaging the virulent virus from about 10 to about 80 times at 30°–38° C. in a tissue culture preparation selected from the group consisting of human and animal diploid cell strains and primary cells of simian origin to attenuate the virus followed by release of the attenuated virus from the infected cell by sonication in the presence of a stabilizer comprising sucrose, albumin, glutamine and phosphate.

2. The process of claim 1 wherein the serial passaging is at 32° C.

3. The process of claim 1 wherein the serial passaging is at 32° C. and 36° C.

4. The process of claim 1 wherein the tissue culture preparation is of human diploid cell strains.

5. The process of claim 4 wherein the human diploid cell strain is human fetal lung tissue.

6. The process of claim 5 wherein the human fetal lung tissue is WI-38.

7. The process of claim 1 wherein the tissue culture preparation is of primary cells of simian origin.

8. The process of claim 7 wherein the primary cells of simian origin are of monkey testicular tissue.

9. The process of claim 1 wherein the tissue culture preparation is of animal diploid cell strain.

10. The process of claim 9 wherein the animal diploid cell strain is of fetal rhesus tissue.

11. The process of claim 6 wherein the stabilizer is SPGA.

12. A live, attenuated cell-free varicella vaccine comprising an immunologically effective amount of a live attenuated cell-free varicella virus prepared by the process of serially passaging the virulent virus from about 10 to about 80 times at 30°–38° C. in a tissue culture preparation selected from the group consisting of human and animal diploid cell strains and primary cells of simian origin to attenuate the virus followed by release of the attenuated virus from the infected cell by sonication in the presence of a stabilizer comprising sucrose, albumin, glutamine and phosphate in combination with a carrier comprising sterile water.

13. The vaccine of claim 10 wherein the serial passaging is at 32° C. and 36° C.

14. The vaccine of claim 12 wherein the tissue culture preparation is of human diploid cell strains.

15. The vaccine of claim 14 wherein the human diploid cell strain is human fetal lung tissue.

16. The vaccine of claim 15 wherein the human fetal lung tissue is WI-38.

17. The vaccine of claim 16 wherein the stabilizer is SPGA.

18. The varicella vaccine of claim 12 is wet-frozen form.

19. The varicella vaccine of claim 12 in lyophilized form.

20. A method of providing immunity against varicella which comprises the administration of the varicella vaccine of claim 12.

* * * * *